United States Patent
Willard

(10) Patent No.: US 9,532,871 B2
(45) Date of Patent: Jan. 3, 2017

(54) DELIVERY SYSTEM DEFLECTION MECHANISM

(71) Applicant: St. Jude Medical, Cardiology Division, Inc., St. Paul, MN (US)

(72) Inventor: Steven N. Willard, Bloomington, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 13/790,132

(22) Filed: Mar. 8, 2013

(65) Prior Publication Data

US 2013/0297012 A1 Nov. 7, 2013

Related U.S. Application Data

(60) Provisional application No. 61/642,889, filed on May 4, 2012.

(51) Int. Cl.
*A61F 2/24* (2006.01)
*A61M 25/01* (2006.01)
*A61M 25/00* (2006.01)

(52) U.S. Cl.
CPC .......... *A61F 2/2427* (2013.01); *A61F 2/2436* (2013.01); *A61M 25/0074* (2013.01); *A61M 25/0133* (2013.01); *A61F 2250/0029* (2013.01)

(58) Field of Classification Search
CPC .. A61F 2/95; A61F 2/2427; A61F 2002/9522; A61F 2002/9665; Y10T 403/32631; Y10T 403/32639; Y10T 403/32672; Y10T 403/32795; Y10T 403/32803; Y10T 403/32975; Y10T 403/32983

(Continued)

(56) References Cited

U.S. PATENT DOCUMENTS 3,384,088 A * 5/1968 Miseo ................. 606/121
3,657,744 A  4/1972 Ersek (Continued)

FOREIGN PATENT DOCUMENTS

EP  1129744 A1  9/2001
EP  1157673 A2  11/2001

(Continued)

OTHER PUBLICATIONS

Ruiz, Carlos, Overview of PRE-CE Mark Transcatheter Aortic Valve Technologies, Euro PCR—dated May 25, 2010.

(Continued)

*Primary Examiner* — Tuan V Nguyen
(74) *Attorney, Agent, or Firm* — Lerner, David, Littenberg, Krumholz & Mentlik, LLP

(57) ABSTRACT

A delivery device for a prosthetic heart valve includes a proximal sheath and a distal sheath. The proximal sheath has a distal end disposed at an oblique angle relative to the longitudinal axis of the proximal sheath, and the distal sheath has a proximal end disposed at an oblique angle relative to the longitudinal axis of the distal sheath. The distal end of the proximal sheath and the proximal end of the distal sheath mate so that rotation of the distal sheath relative to the proximal sheath causes the distal sheath to deflect from coaxial alignment with the proximal sheath. Deflection of the distal sheath relative to the proximal sheath enables the prosthetic valve to be axially aligned with the native valve annulus for deployment.

20 Claims, 6 Drawing Sheets

(58) Field of Classification Search
USPC ...... 623/2.11, 1.11; 606/108, 158, 159, 167, 606/170, 194, 198

See application file for complete search history.

(56) References Cited

U.S. PATENT DOCUMENTS

| | | | |
|---|---|---|---|
| 3,724,238 A * | 4/1973 | Retali | B04B 9/12 |
| | | | 34/58 |
| 4,423,730 A | 1/1984 | Gabbay | |
| 4,641,657 A * | 2/1987 | Ellis | 606/1 |
| 5,368,592 A | 11/1994 | Stern et al. | |
| 5,372,587 A | 12/1994 | Hammerslag et al. | |
| 5,405,344 A * | 4/1995 | Williamson et al. | 606/1 |
| 5,507,725 A | 4/1996 | Savage et al. | |
| 5,549,594 A | 8/1996 | Brunken | |
| 5,569,270 A * | 10/1996 | Weng | 606/144 |
| 5,575,799 A * | 11/1996 | Bolanos | A61B 17/0684 |
| | | | 227/175.1 |
| 5,749,881 A * | 5/1998 | Sackier et al. | 606/151 |
| 5,843,167 A | 12/1998 | Dwyer et al. | |
| 5,868,685 A * | 2/1999 | Powell et al. | 600/585 |
| 5,924,424 A | 7/1999 | Stevens et al. | |
| 5,968,068 A | 10/1999 | Dehdashtian et al. | |
| 6,077,297 A | 6/2000 | Robinson et al. | |
| 6,183,432 B1 * | 2/2001 | Milo | A61B 17/22012 |
| | | | 604/22 |
| 6,306,141 B1 | 10/2001 | Jervis | |
| 6,464,684 B1 | 10/2002 | Galdonik | |
| 6,599,237 B1 * | 7/2003 | Singh | A61B 1/0008 |
| | | | 600/114 |
| 6,623,518 B2 | 9/2003 | Thompson et al. | |
| 6,743,239 B1 | 6/2004 | Kuehn et al. | |
| 6,814,746 B2 | 11/2004 | Thompson et al. | |
| 6,830,584 B1 | 12/2004 | Seguin | |
| 7,018,406 B2 | 3/2006 | Seguin et al. | |
| 7,300,431 B2 * | 11/2007 | Dubrovsky | 606/1 |
| 7,311,730 B2 | 12/2007 | Gabbay | |
| 7,510,572 B2 | 3/2009 | Gabbay | |
| 7,637,905 B2 | 12/2009 | Saadat et al. | |
| 7,682,390 B2 | 3/2010 | Seguin | |
| 7,803,185 B2 | 9/2010 | Gabbay | |
| 7,811,277 B2 | 10/2010 | Boulais | |
| 9,227,990 B2 | 1/2016 | Phull et al. | |
| 2003/0050694 A1 | 3/2003 | Yang et al. | |
| 2003/0233108 A1 * | 12/2003 | Gellman et al. | 606/144 |
| 2004/0210304 A1 | 10/2004 | Seguin et al. | |
| 2005/0137622 A1 * | 6/2005 | Griffin | 606/198 |
| 2005/0137695 A1 | 6/2005 | Salahieh et al. | |
| 2005/0137697 A1 | 6/2005 | Salahieh et al. | |
| 2005/0165352 A1 * | 7/2005 | Henry | A61F 2/95 |
| | | | 604/108 |
| 2005/0177138 A1 * | 8/2005 | Dubrovsky | A61B 17/29 |
| | | | 606/1 |
| 2005/0222604 A1 | 10/2005 | Schaeffer | |
| 2006/0058872 A1 | 3/2006 | Salahieh et al. | |
| 2006/0074484 A1 | 4/2006 | Huber | |
| 2006/0100687 A1 | 5/2006 | Fahey et al. | |
| 2006/0106415 A1 | 5/2006 | Gabbay | |
| 2006/0142848 A1 | 6/2006 | Gabbay | |
| 2006/0167468 A1 | 7/2006 | Gabbay | |
| 2006/0235502 A1 | 10/2006 | Belluche et al. | |
| 2006/0259120 A1 | 11/2006 | Vongphakdy et al. | |
| 2007/0010876 A1 | 1/2007 | Salahieh et al. | |
| 2007/0027534 A1 | 2/2007 | Bergheim et al. | |
| 2007/0043259 A1 | 2/2007 | Jaffe et al. | |
| 2007/0043435 A1 | 2/2007 | Seguin et al. | |
| 2007/0055358 A1 | 3/2007 | Krolik et al. | |
| 2007/0073376 A1 * | 3/2007 | Krolik et al. | 623/1.11 |
| 2007/0073391 A1 | 3/2007 | Bourang et al. | |
| 2007/0088431 A1 | 4/2007 | Bourang et al. | |
| 2007/0112422 A1 | 5/2007 | Dehdashtian | |
| 2007/0162100 A1 | 7/2007 | Gabbay | |
| 2007/0168013 A1 | 7/2007 | Douglas | |
| 2007/0203575 A1 | 8/2007 | Forster et al. | |
| 2007/0239271 A1 | 10/2007 | Nguyen | |
| 2007/0244552 A1 | 10/2007 | Salahieh et al. | |
| 2007/0250113 A1 | 10/2007 | Hegeman et al. | |
| 2008/0065122 A1 * | 3/2008 | Stack | A61B 17/00234 |
| | | | 606/151 |
| 2008/0071369 A1 | 3/2008 | Tuval et al. | |
| 2008/0147160 A1 | 6/2008 | Ghione et al. | |
| 2008/0147182 A1 | 6/2008 | Righini et al. | |
| 2008/0228223 A1 * | 9/2008 | Alkhatib | 606/221 |
| 2009/0054975 A1 | 2/2009 | del Nido et al. | |
| 2009/0062606 A1 | 3/2009 | Ueda et al. | |
| 2009/0062839 A1 | 3/2009 | Kurrus | |
| 2010/0004740 A1 | 1/2010 | Seguin et al. | |
| 2010/0204708 A1 | 8/2010 | Sharma | |
| 2010/0228152 A1 | 9/2010 | Fisher et al. | |
| 2010/0228191 A1 | 9/2010 | Alvarez et al. | |
| 2010/0286768 A1 | 11/2010 | Alkhatib | |
| 2010/0298931 A1 | 11/2010 | Quadri et al. | |
| 2011/0098800 A1 | 4/2011 | Braido et al. | |
| 2011/0207999 A1 | 8/2011 | Torisawa et al. | |
| 2011/0224678 A1 | 9/2011 | Gabbay | |
| 2011/0245917 A1 | 10/2011 | Savage et al. | |
| 2012/0078350 A1 | 3/2012 | Wang et al. | |
| 2012/0303111 A1 | 11/2012 | Dwork et al. | |
| 2013/0060328 A1 | 3/2013 | Rothstein | |
| 2013/0103047 A1 | 4/2013 | Steingisser et al. | |
| 2013/0274870 A1 | 10/2013 | Lombardi et al. | |
| 2013/0297012 A1 * | 11/2013 | Willard | 623/2.11 |
| 2013/0297102 A1 | 11/2013 | Hughes et al. | |

FOREIGN PATENT DOCUMENTS

| | | |
|---|---|---|
| EP | 1716822 A1 | 11/2006 |
| EP | 1926455 A2 | 6/2008 |
| FR | 2765098 A1 | 12/1998 |
| WO | 9510317 A1 | 4/1995 |
| WO | 2006138173 A2 | 12/2006 |
| WO | 2007071436 A2 | 6/2007 |
| WO | 2008070797 A2 | 6/2008 |
| WO | 2010051025 A1 | 5/2010 |
| WO | 2010087975 A1 | 8/2010 |
| WO | 2010127162 A1 | 11/2010 |
| WO | 2012112469 A2 | 8/2012 |
| WO | 2013166355 A1 | 11/2013 |
| WO | 2014130160 A1 | 8/2014 |

OTHER PUBLICATIONS

Quaden, Rene et al., Percutaneous aortic valve replacement: resection before implantation, 836-840, European J. of Cardio-thoracic Surgery, 27 (2005).

International Search Report for Application No. PCT/US2013/078306 dated May 2, 2014.

International Search Report and Written Opinion for Application No. PCT/US2013/039405 dated Sep. 23, 2013.

International Search Report and Written Opinion for Application No. PCT/US2014/054025 dated Nov. 19, 2014.

International Search Report and Written Opinion for Application No. PCT/US2014/055053 dated Nov. 24, 2014.

\* cited by examiner

DELIVERY SYSTEM DEFLECTION MECHANISM

CROSS REFERENCE TO RELATED APPLICATION

The application claims the benefit of the filing date of U.S. Provisional Patent Application No. 61/642,889 filed May 4, 2012, the disclosure of which is hereby incorporated herein by reference.

BACKGROUND OF THE INVENTION

The present invention is related to heart valve replacement, and more particularly to devices, systems, and methods for transcatheter delivery of collapsible prosthetic heart valves.

Prosthetic heart valves that are collapsible to a relatively small circumferential size may be delivered into a patient less invasively than valves that are not collapsible. For example, a collapsible valve may be delivered into a patient via a tube-like delivery apparatus such as a catheter, a trocar, a laparoscopic instrument, or the like. This collapsibility may avoid the need for a more invasive procedure such as full open-chest, open-heart surgery.

Collapsible prosthetic heart valves typically take the form of a valve structure mounted on a stent. To place such a valve into a delivery apparatus and ultimately into a patient, the valve must first be collapsed or crimped to reduce its circumferential size. For example, a conventional collapsible prosthetic valve is typically collapsed and retained in a collapsed state by a sheath for delivery into the patient, for example, through a femoral artery or through the apex of the heart.

An end of a guide wire may be inserted percutaneously into the artery or the heart of a patient just beyond a desired implant site to establish a guide for an implantable delivery device to follow. The desired implant site is often at or near the annulus of the patient's heart valve that is to be replaced by the prosthetic valve. Once the delivery apparatus containing the prosthetic valve has reached this site, the valve may be deployed or released from the delivery apparatus and re-expanded to full operating size. For self-expanding valves, the stent automatically begins to expand as the sheath covering the valve is withdrawn.

In certain transapical delivery systems employing self-expanding aortic valves, for example, after the delivery system has been positioned for deployment, the annulus end of the valve may be unsheathed and expanded first, while the aortic end of the valve remains sheathed. Once the annulus end of the valve has expanded, it may be determined that the valve needs to be repositioned in the patient's aortic annulus. To accomplish this, the user (such as a surgeon or an interventional cardiologist) may resheath the annulus end of the valve so that the valve can be repositioned while in a collapsed state. After the valve has been repositioned, the user can again deploy the valve.

Despite the various improvements that have been made to the collapsible prosthetic heart valve delivery process, conventional delivery devices, systems, and methods suffer from some shortcomings. For example, in a conventional delivery device for collapsible prosthetic valves, such as a transapical delivery device 7 shown in FIG. 1, because the aortic valve is not directly aligned with the apex of the heart, it may be difficult to align the longitudinal axis of the distal sheath 8 normally to the geometric center of the native valve annulus 6 (i.e., axial alignment). Without axial alignment, the user will be unable to properly position the prosthetic valve relative to the native annulus 6, such that the valve will not be properly seated in the annulus and therefore will not function properly. Moreover, without axial alignment, the inner wall 3 of the aortic arch 2 may interfere with the advancement of delivery device 7 beyond the native valve annulus 6, and contact between the distal tip 9 of the delivery device and the inner wall of the aortic arch may damage the aorta.

There is therefore a need for further improvements to the devices, systems, and methods for transcatheter delivery of collapsible prosthetic heart valves. Among other advantages, the present invention may address one or more of these needs.

BRIEF SUMMARY OF THE INVENTION

One aspect of the present invention provides a device for delivering a medical implant into a patient. One embodiment of the delivery device includes a first sheath having a proximal end, a distal end and a longitudinal axis, the distal end having a surface disposed at an oblique angle relative to the longitudinal axis of the proximal sheath; and a distal sheath connected to the distal end of the proximal sheath, the distal sheath having a proximal end, a distal end and a longitudinal axis. The proximal end of the distal sheath has a surface disposed at an oblique angle relative to the longitudinal axis of the distal sheath, the proximal end surface of the distal sheath being in mating engagement with the distal end surface of the proximal sheath. The distal sheath is rotatable relative to the proximal sheath from a first position in which the longitudinal axis of the distal sheath is substantially coaxial with the longitudinal axis of the proximal sheath, to a second position in which the longitudinal axis of the distal sheath is oriented at an oblique angle to the longitudinal axis of the proximal sheath. The oblique angle at which the distal end surface of the proximal sheath is oriented is preferably the same as the oblique angle at which the proximal end surface of the distal sheath is oriented. The distal sheath may be rotated by at least about 180° from the first position to the second position. An atraumatic tip may be connected to the distal end of the distal sheath.

The proximal sheath may be rotatably connected to the distal sheath by an axle. One end of the axle may be fixedly connected to one of the proximal sheath or distal sheath, while the other end of the axle may be rotatably connected to the other of the proximal sheath or distal sheath. Alternatively, both ends of the axle may be rotatably connected to the respective sheaths. Rather than an axle, the proximal sheath may be connected to the distal sheath by a ball-and-socket connection.

The device may further include a locking mechanism having a first position permitting rotation of the distal sheath relative to the proximal sheath, and a second position preventing rotation of the distal sheath relative to the proximal sheath. The locking mechanism may include an elongated member movable in the proximal sheath between a retracted position and an extended position, and at least one recess in the distal sheath, the elongated member in the extended position being receivable in the recess to prevent rotation of the distal sheath relative to the proximal sheath, and the elongated member in the retracted position being free of the recess to permit rotation of the distal sheath relative to the proximal sheath. A spring may be disposed on the elongated member for biasing the elongated member to the extended position.

The proximal sheath may include a lumen extending between the proximal end of the proximal sheath and the distal end of the proximal sheath, and the distal sheath may include a lumen extending between the proximal end of the distal sheath and the distal end of the distal sheath, the lumen of the proximal sheath being in communication with the lumen of the distal sheath.

One or both of the distal end surface of the proximal sheath and the proximal end surface of the distal sheath may be flat, curvate, hemispheroidal, or any other desired shape.

Another aspect of the present invention provides a method for implanting a prosthetic heart valve into a patient. The method includes inserting a delivery device into the patient, the delivery device including a proximal sheath, a distal sheath and a prosthetic heart valve assembled in the distal sheath. The proximal sheath has a proximal end, a distal end and a longitudinal axis, the distal end having a surface disposed at an oblique angle relative to the longitudinal axis of the proximal sheath. The distal sheath is connected to the distal end of the proximal sheath, and has a proximal end, a distal end and a longitudinal axis. The proximal end of the distal sheath has a surface disposed at an oblique angle relative to the longitudinal axis of the distal sheath, the proximal end surface of the distal sheath being in mating engagement with the distal end surface of the proximal sheath. The method further includes rotating the distal sheath relative to the proximal sheath to orient the longitudinal axis of the distal sheath at an oblique angle to the longitudinal axis of the proximal sheath; and deploying the prosthetic heart valve from the distal sheath.

The proximal sheath may have a lumen extending from the proximal end of the proximal sheath to the distal end of the proximal sheath, and the distal sheath may have a lumen extending from the proximal end of the distal sheath to the distal end of the distal sheath. In such event, the method may further include inserting a guidewire into the patient; and inserting the delivery device over the guidewire by passing the guidewire through the lumen in the distal sheath and the lumen in the proximal sheath.

BRIEF DESCRIPTION OF THE DRAWINGS

Various embodiments of the present invention will now be discussed with reference to the appended drawings. It is to be appreciated that these drawings depict only some embodiments of the invention and are therefore not to be considered limiting of its scope.

DETAILED DESCRIPTION

In the present application, reference is made to particular features of the invention. It is to be understood that the disclosure of the invention in this application is intended to include all possible combinations of such features, whether or not such combinations have been particularly described. For example, where a feature is disclosed in the context of a particular aspect, arrangement, or embodiment of the invention, that feature can also be used, to the extent possible, in combination with and/or in the context of other aspects, arrangements, and embodiments of the invention described herein.

The term "comprises" and grammatical equivalents thereof are used herein to mean that other components, ingredients, steps, etc. are optionally present. For example, an article "comprising" (or "which comprises") components A, B, and C can consist of (i.e., contain) only components A, B, and C, or can consist of not only components A, B, and C, but also one or more other components. The term "step of" does not mean "step for".

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all of the defined steps (except where the context excludes that possibility).

The term "at least" followed by a number is used herein to denote the start of a range beginning with that number (which can be a range having an upper limit or no upper limit, depending on the variable being defined). For example, "at least 1" means 1 or more than 1.

As used herein, the terms "proximal" and "distal" are to be taken as relative to a user (e.g., a surgeon or an interventional cardiologist) of the disclosed delivery devices. "Proximal" is to be understood as relatively close to the user and "distal" is to be understood as relatively farther away from the user.

As described further herein, a device for delivering collapsible prosthetic heart valves (or other types of collapsible stents) in accordance with the present invention may include a catheter having proximal and distal portions, the longitudinal axis of the distal portion being substantially coaxial with the longitudinal axis of the proximal portion in one position, and being oriented at varying oblique angles to the longitudinal axis of the proximal portion in other positions to enable the device to deliver a prosthetic heart valve in substantial axial alignment with the native annulus in which the valve is to be deployed.

Figure 1:
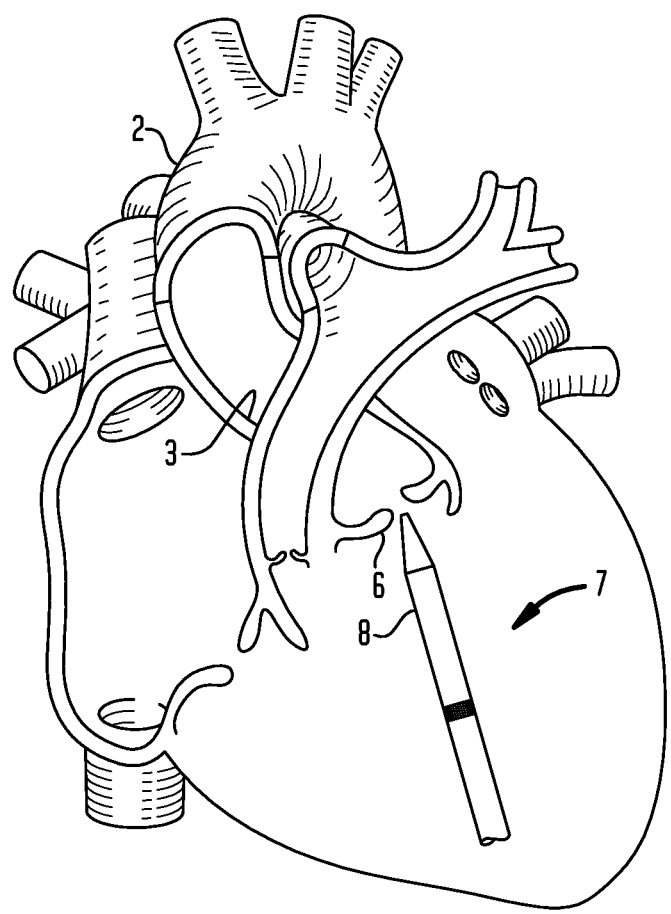
FIG. 1 is a diagrammatic view showing the use of a conventional transapical delivery device to deliver a collapsible prosthetic heart valve to the aortic valve annulus.
Figure 2:
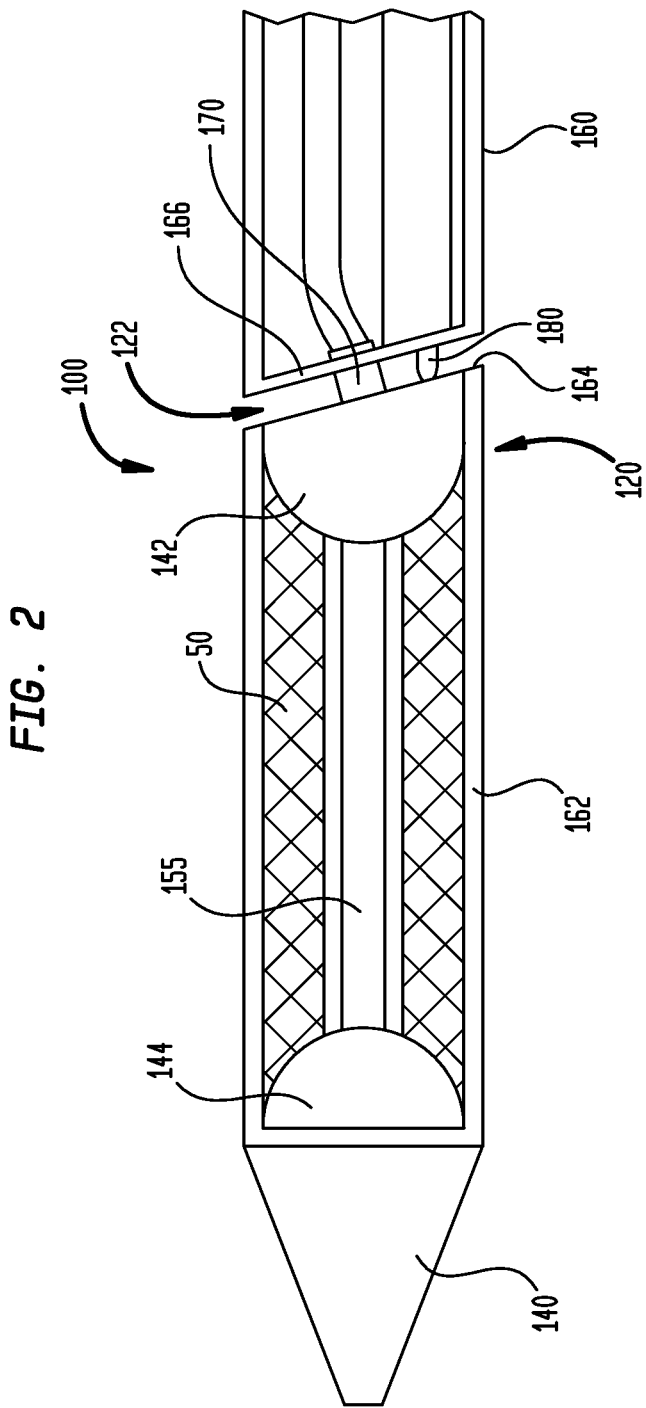
FIG. 2 is a plan view of a distal portion of a delivery device in accordance with one embodiment of the present invention, shown in partial cross-section in a substantially straight configuration.
Figure 3:
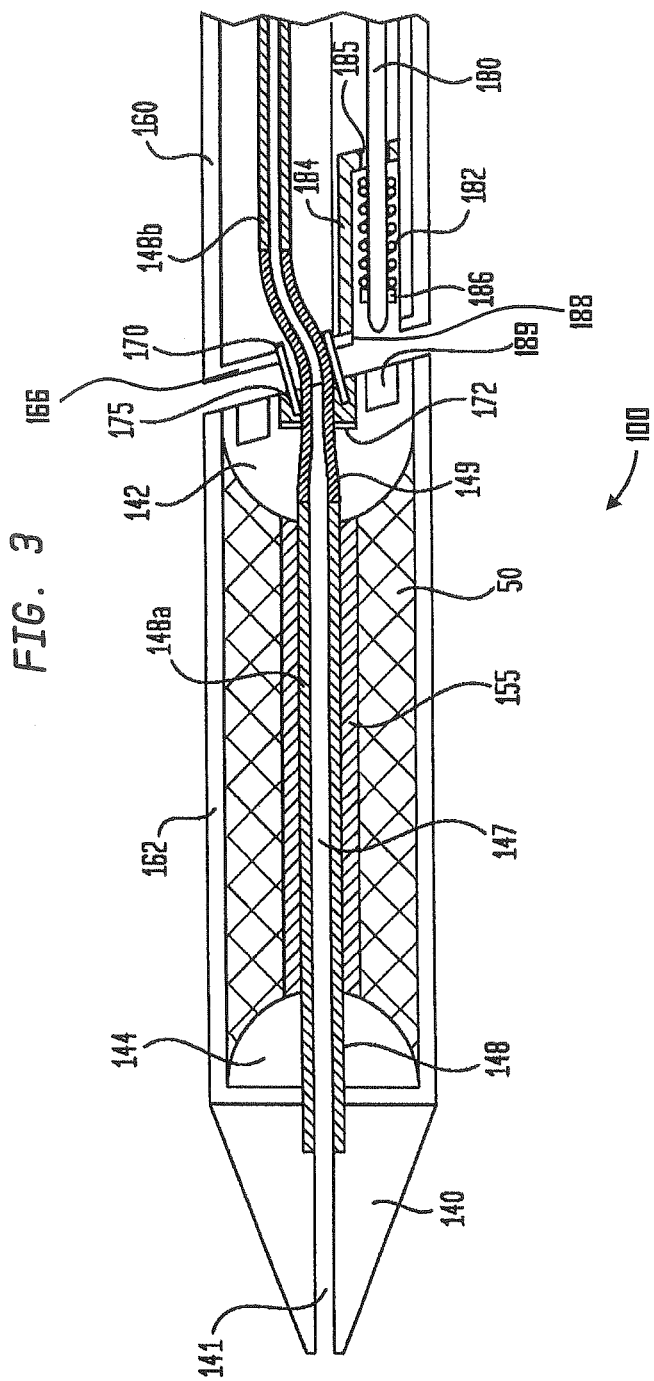
FIG. 3 is a cross-sectional plan view of the distal portion of the delivery device of FIG. 2, shown in the substantially straight configuration.
Figure 4:
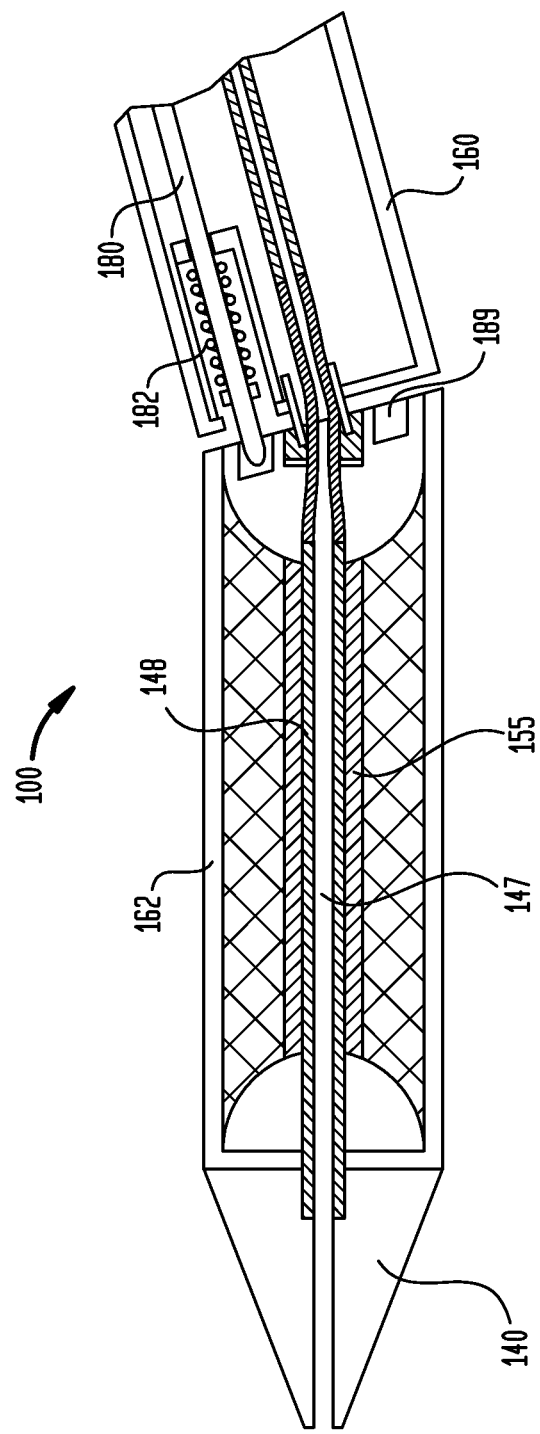
FIG. 4 is a cross-sectional plan view of the distal portion of the delivery device of FIG. 2, shown in a deflected configuration.

Referring now to FIGS. 2-4, in one embodiment of the invention, a delivery device 100 may include a hollow elongated sheath 120 having a longitudinal axis extending between its proximal end (not shown) and its distal end. The sheath 120 may have a circular cross-section as shown, or any other cross-section as desired, such as an elliptical cross-section. Sheath 120 may have a "split sheath" configuration, i.e., it may be separated, as at 122, into a proximal sheath 160 and a distal sheath 162. As will be explained below, the distal sheath 162 may be moved distally relative to the proximal sheath 160 in order to deploy the prosthetic valve.

At its distal end, device 100 may include a proximal retainer 142 and a distal retainer 144 spaced apart by a hollow shaft 155 so as to define a receiving compartment therebetween. An implantable device, such as a collapsible prosthetic heart valve 50, may be mounted in the receiving compartment around shaft 155. As illustrated in FIGS. 2-4, the distal sheath 162 may act as a covering over the valve 50. The distal end of the proximal sheath 160 may be closed by an end wall 166 disposed at an oblique angle relative to the longitudinal axis of the proximal sheath. The proximal end 164 of the distal sheath 162 may similarly be disposed at an oblique angle relative to the longitudinal axis of the distal sheath, but is not enclosed by an end wall so that the distal sheath is able to move distally to deploy valve 50. Preferably, the proximal end 164 of distal sheath 162 will be oriented at substantially the same angle as the end wall 166 of proximal sheath 160. In a variant hereof, the proximal end 164 of distal sheath 162 may be closed by the proximal retainer 142. In such event, the proximal surface of proximal retainer 142 may lie at an oblique angle to the longitudinal axis of distal sheath 162 so as to lie in the same plane as the proximal end 164 of the distal sheath. Although sheath end wall 166 and the proximal end 164 of distal sheath 162 are depicted as planar, they may be curvate, hemispheroidal or any other desired shape.

An atraumatic tip 140 formed from a soft polymer may be fixedly connected to the distal end of distal sheath 162. The tip 140 may have a cross-section that matches the cross-section of distal sheath 162. An inner tubular shaft 148 may be connected at one end to tip 140, and may extend through hollow shaft 155 and through proximal sheath 160 to the proximal end thereof. Shaft 148 has a central lumen 147 which communicates with a bore 141 extending longitudinally through tip 140. Lumen 147 and bore 141 together define a channel through device 100 for a guidewire (not shown). Preferably, lumen 147 remains patent through shaft 148 whether the longitudinal axes of proximal sheath 160 and distal sheath 162 are coaxially aligned, or are disposed at an oblique angle to one another, thereby enabling device 100 to be advanced over the guidewire in either a coaxial or angularly deflected configuration. Pushing inner shaft 148 in a distal direction will cause distal sheath 162 to slide distally to an open position relative to proximal sheath 160, and pulling inner shaft 148 in a proximal direction will cause the distal sheath to slide proximally to a closed position relative to the proximal sheath.

In the fully closed position, the distal sheath 162 may be in a proximalmost position covering the valve 50 with its proximal end 164 abutting the end wall 166 of the proximal sheath 160. In the fully opened position, the distal sheath 162 may be in a distalmost position with its proximal end 164 spaced from the end wall 166 of the proximal sheath to expose the prosthetic valve 50 for deployment. Although the figures illustrate a gap between the proximal end 164 of distal sheath 162 and end wall 166 in the closed position of the distal sheath, that gap is merely for the purpose of illustrating the various components of device 100. Thus, in the fully closed position, the proximal end 164 of distal sheath 162 and end wall 166 will preferably be in abutting relationship as will be described further below.

The proximal sheath 160 and the distal sheath 162 may be connected by a tubular axle 170. As clearly seen in FIG. 2, the longitudinal axis of axle 170 preferably is oriented substantially perpendicular to sheath ends 164 and 166 so as to not interfere with the rotation of sheaths 160 and 162 relative to one another. The central bore extending through axle 170 has a diameter sufficient to slidably receive inner shaft 148 therethrough. One end of axle 170 may be connected to sheath end wall 166 and the other end may be connected to proximal retainer 142, the connection being made so that at least one end of the axle is freely rotatable. Thus, for example, one end of axle 170 may be fixedly connected to sheath end wall 166, while the other end is rotatably connected to retainer 142. Optionally, the rotatable end of axle 170 may be journaled in a receiving element, such as roller bearing 175, disposed in the retainer 142. A flange 172 at an end of axle 170 may maintain the assembly between the axle and roller bearing 175. It will be appreciated, of course, that in a variant hereof, one end of the axle may be fixedly connected to retainer 142 and the end of the axle connected to end wall 166 may be rotatable, and that the roller bearing 175 or other retaining element may be mounted to the end wall 166 to facilitate rotation.

Device 100 may further include a locking rod 180 which extends along the length of proximal sheath 160 in a position offset from the central axis thereof. A compression spring 182 may be assembled around the distal end of rod 180 and constrained between an end member 185 of a spring retainer 184 mounted to the sheath end wall 166 and a stop ring 186 fixedly mounted to the locking rod. Spring 182 may bias locking rod 180 distally so that the distal end thereof projects through an aperture 188 in the sheath end wall 166, and into one of a series of recesses 189 in the proximal retainer 142. The engagement of locking rod 180 in one of recesses 189 fixes the rotational position of distal sheath 162 relative to the proximal sheath 160. Preferably, retainer 142 includes an appropriate number of recesses 189 along its outer periphery to lock the distal sheath 162 at any number of desired rotational angles relative to the proximal sheath 160. The size of spring 182 is selected so that locking rod 180 may be retracted by an amount sufficient to move the distal end of the rod out from a recess 189, thereby freeing the distal sheath 162 to rotate relative to proximal sheath 160.

In an initial fully closed position, shown in FIG. 3, the proximal sheath 160 and the distal sheath 162 may share a common longitudinal axis. Upon retraction of locking rod 180, the distal sheath 162 may be rotated relative to the proximal sheath 160 about the longitudinal axis of axle 170. As a result of the oblique angle defined between the two sheaths, rotation of the distal sheath 162 relative to the proximal sheath 160 will cause the longitudinal axis of the distal sheath to deflect away from coaxial alignment with the longitudinal axis of the proximal sheath.

The angle formed by the intersection of the longitudinal axes of the distal sheath 162 and the proximal sheath 160 increases or decreases as the sheaths are rotated relative to one another. When the end wall 166 of the proximal sheath 160 and the proximal end 164 of the distal sheath 162 are both flat and disposed at the same oblique angle to the longitudinal axes of their respective sheaths, the maximum angular displacement between the longitudinal axes will occur when the sheaths have been rotated from their coaxial configuration 180° relative to one another. The amount of angular displacement achieved preferably is at least about 15°. However, the angular displacement should be sufficient to enable the distal sheath 162 to be substantially axially aligned with the native aortic annulus. When the oblique angles at which the proximal end 164 of distal sheath 162 and the sheath end wall 166 are disposed are about equal, the maximum angular displacement that may be achieved will be about twice the oblique angle. Thus, for example, when the oblique angle is about 15°, the maximum angular displacement achieved when the distal sheath 162 is rotated 180° relative to the proximal sheath 160 will be about 30°.

It will be appreciated that the maximum angular displacement which device 100 may achieve may be increased by increasing the oblique angle of at least one of proximal end 164 or end wall 166 relative to the longitudinal axes of their respective sheaths. However, if the oblique angles are not equal, coaxial alignment will be difficult to achieve, if achievable at all.

In order for distal sheath 162 to become angularly displaced relative to proximal sheath 160, it is necessary for inner shaft 148 to be able to bend at the interface between the sheaths. It will be appreciated that this may be accomplished in any number of ways while still maintaining the ability of inner shaft 148 to control the longitudinal movement of distal sheath 162 relative to proximal sheath 160. For example, inner shaft 148 may be formed from first and second substantially rigid portions 148a, 148b joined together by a relatively stiff spring, a length of polymer tubing or another flexible tubular material 149 which will enable the rigid portions to move at substantially any angle relative to one another. Alternatively, the rigid portions may be joined together by a ball and socket joint (not shown) which similarly will provide for unlimited angular displacement between the rigid shaft lengths. Thus, the substantially rigid portions of shaft 148 may be connected by any joint that will enable the portions of the shaft to be deflected from substantially coaxial alignment, but that will still retain sufficient strength in both compression and tension to displace distal sheath 162 longitudinally relative to proximal sheath 160.

The delivery device 100 may be inserted into a patient during a minimally invasive surgical procedure such as, for example, to replace a native heart valve with a collapsible prosthetic heart valve. During a transapical surgical procedure to replace the native aortic valve, device 100 may be locked in the straight or coaxial position and inserted through the apex of the heart and the left ventricle and advanced toward the native aortic valve. As the distal tip 140 of device 100 contacts the aortic annulus 6, locking rod 180 may be retracted until the distal end thereof is fully removed from recess 189 in proximal retainer 142, freeing the distal sheath 162 for rotation relative to the proximal sheath 160. As the proximal sheath 160 is rotated by the user, friction between distal tip 140 and the native valve annulus 6 will inhibit the rotation of distal sheath 162. As a result, proximal sheath 160 will rotate relative to distal sheath 162, thereby deflecting the longitudinal axis of distal sheath 162 relative to the longitudinal axis of proximal sheath 160. Locking rod 180 may then be released, whereupon spring 182 will bias the rod through aperture 188 and into a different recess 189 in proximal retainer 142. The creation of an angle between proximal sheath 160 and distal sheath 162 will enable the distal tip 140 to be directed away from the native valve annulus 6 and the interior wall 3 of aortic arch 2, and will enable device 100 to be advanced further into and through the native valve annulus. As device 100 is advanced, the distal tip 140 will again approach the interior wall 3 of aortic arch 2, and the locking rod 180 may again be retracted and proximal sheath 160 rotated relative to distal sheath 162 to increase the angle between the longitudinal axes of the sheaths. Locking rod 180 may then be released to engage a different recess 189, locking the sheaths relative to one another in this new position. This procedure may be repeated as device 100 is advanced through aortic annulus 6 until distal sheath 162 is substantially in axial alignment with the native valve annulus and sufficiently advanced therethrough for deployment of valve 50. Following deployment, the procedure may be reversed, perhaps with fewer increments, to remove device 100 from the patient. Although the foregoing describes incremental rotations between distal sheath 162 and proximal sheath 160 as device 100 is advanced into and through aortic annulus 6, it will be appreciated that the procedure may be accomplished with only a single 180° rotation of the sheaths relative to one another. In such event, device 100 may be configured so as to be lockable in only two positions, namely, a coaxial position and a position rotated 180° from the coaxial position.

Figure 5:
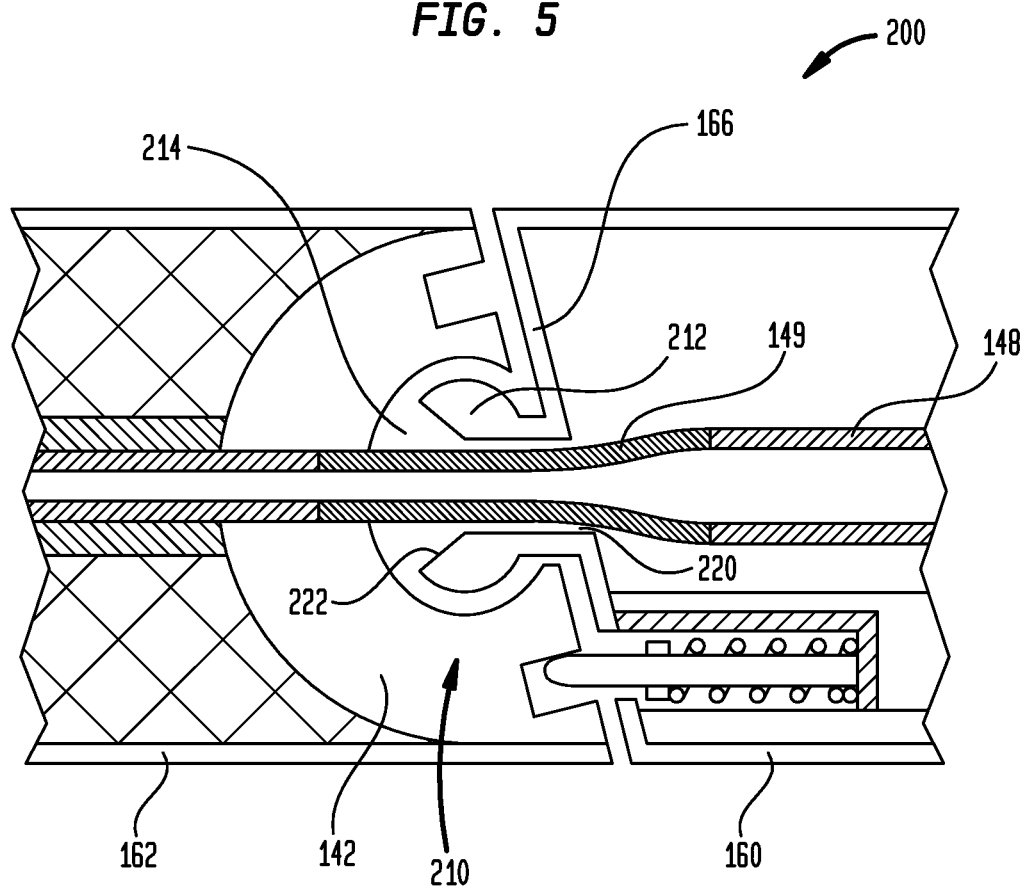
FIG. 5 is a cross-sectional plan view of a portion of a delivery device in accordance with another embodiment of the present invention, shown in a substantially straight configuration.
Figure 6:
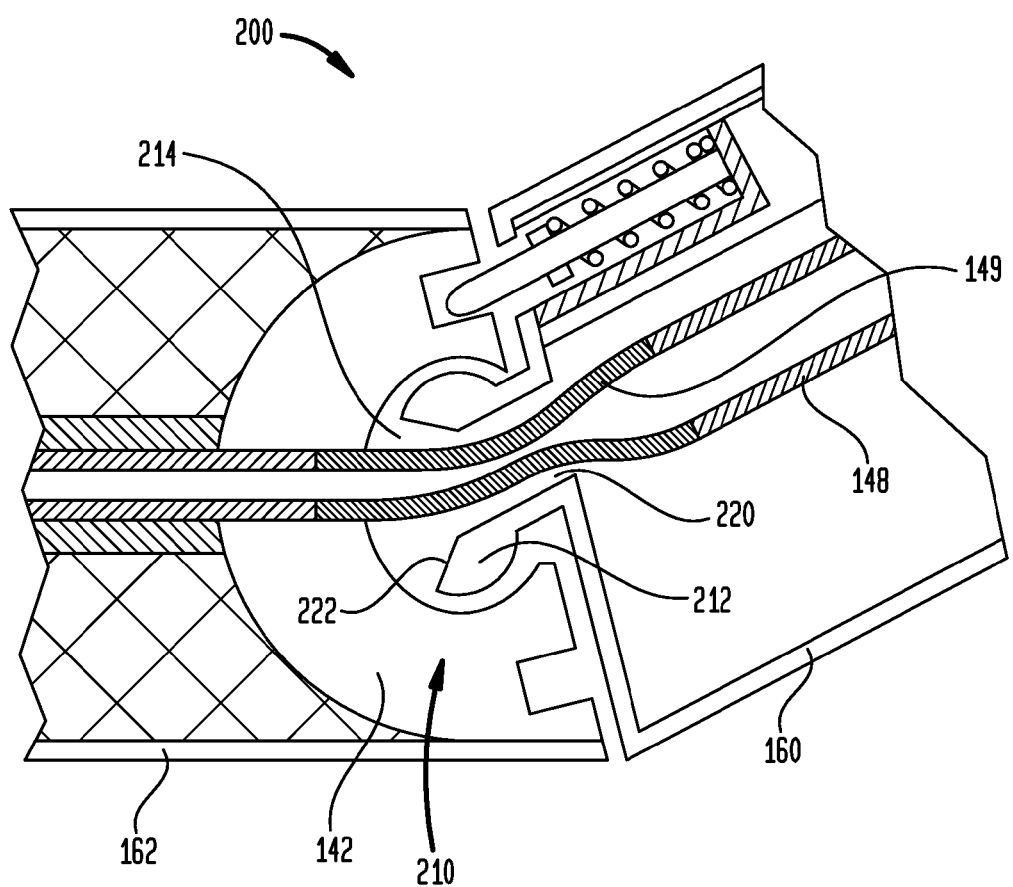
FIG. 6 is a cross-sectional plan view of the portion of the delivery device of FIG. 5, shown in a deflected configuration.

An alternate embodiment of a delivery device 200 is shown in FIGS. 5 and 6. Delivery device 200 is substantially the same as delivery device 100 described above. However, rather than employing an axle 170 to rotatably connect distal sheath 162 to proximal sheath 160, device 200 employs a ball and socket connection 210. Thus, a ball 212 may project from the end wall 166 of proximal sheath 160 and be received within a socket 214 formed in proximal retainer 142. Ball 212 may include a throughbore 220 sized to slidably receive inner shaft 148 therethrough. At the free end of ball 212, throughbore 220 may have an outwardly flared or chamfered surface 222. Surface 222 will accommodate the bending of inner shaft 148 as distal sheath 162 is deflected relative to proximal sheath 160, and will prevent the flexible portion 149 of the shaft from kinking or becoming pinched closed as shaft 148 bends. In a variant hereof, the components of ball and socket connection 210 may be reversed. That is, ball 212 may be connected to proximal retainer 142 and socket 214 may be formed in or connected to sheath end wall 166.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A device for delivering an implantable medical apparatus into a patient, the device comprising:
    a shaft having proximal and distal ends and a longitudinal axis, the distal end having a surface disposed at an oblique angle relative to the longitudinal axis of the shaft;
    a tip operatively connected to the distal end of the shaft, the tip having a proximal end, a distal end and a longitudinal axis, the proximal end of the tip having a surface disposed at an oblique angle relative to the longitudinal axis of the tip, the proximal end surface of the tip being in mating engagement with the distal end surface of the shaft, the tip having a rotation axis perpendicular to the distal end surface of the shaft and the proximal end surface of the tip so that the tip is rotatable from a first position in which the longitudinal axis of the tip is collinear with the longitudinal axis of the shaft to a second position in which the longitudinal axis of the tip is oriented at an oblique angle relative to the longitudinal axis of the shaft, the tip defining a compartment adapted to receive the medical apparatus between the proximal end of the tip and the distal end of the tip; and
    a sheath connected to the tip and movable with the tip between the first position and the second position, the sheath being movable distally away from the distal end of the shaft from a first condition in which the sheath encloses the compartment to a second condition in which the sheath exposes the compartment for deployment of the medical apparatus into the patient.

2. The device of claim 1, wherein the tip is rotatable at least 180 degrees from the first position to the second position.

3. The device of claim 1, further comprising:
a locking mechanism attached to the shaft, the locking mechanism having a first position permitting rotation of the tip relative to the shaft, and a second position preventing rotation of the tip relative to the shaft.

4. The device of claim 3, wherein the locking mechanism includes an elongated member movable in the shaft between a retracted position and an extended position, and an aperture in the tip, the elongated member in the extended position being received in the aperture to prevent rotation of the tip relative to the shaft, and the elongated member in the retracted position being free of the aperture to permit rotation of the tip relative to the shaft.

5. The device of claim 4, further comprising a spring disposed on the elongated member for biasing the elongated member to the extended position.

6. The device of claim 1, wherein the shaft includes a lumen extending between the proximal end and the distal end of the shaft, and the tip includes a lumen extending between the proximal end and the distal end of the tip, the shaft lumen being in communication with the tip lumen.

7. The device of claim 1, further comprising:
an axle connecting the tip to the shaft.

8. The device of claim 7, wherein a longitudinal axis of the axle is at an oblique angle relative to the longitudinal axis of the shaft or the tip.

9. The device of claim 7, wherein the axle connects the distal end of the shaft to the proximal end of the tip and either the shaft or the tip rotates about the axle such that the axle defines the rotation axis.

10. The device of claim 1, wherein the proximal end surface of the tip and the distal end surface of the shaft are substantially parallel during rotation of the tip from the first position to the second position.

11. A device for delivering an implantable medical apparatus into a patient, the device comprising:
a shaft having proximal and distal portions along a longitudinal axis, the distal portion having a planar end surface;
a tip having a distal end, a planar end surface at a proximal end thereof and a longitudinal axis, the planar end surface of the tip being adjacent to and facing the planar end surface of the distal portion of the shaft, the tip defining a compartment adapted to receive the medical apparatus between the proximal end of the tip and the distal end of the tip;
a ball-and-socket combination interconnecting the shaft and the tip; and
a sheath movable distally away from the distal end of the shaft from a first condition in which the sheath encloses the compartment to a second condition in which the sheath exposes the compartment for deployment of the medical apparatus into the patient,
wherein the tip has a rotation axis perpendicular to the planar end surface of the shaft and the planar end surface of the tip so that the tip is rotatable from a first position in which the longitudinal axis of the tip is collinear with the longitudinal axis of the shaft to a second position in which the longitudinal axis of the tip is oriented at an oblique angle relative to the longitudinal axis of the shaft, the sheath being movable with the tip between the first position and the second position, and
wherein the planar end surfaces of the tip and the distal portion of the shaft are substantially parallel during rotation of the tip from the first position to the second position.

12. The device of claim 11, wherein a first lumen passes through the shaft, a second lumen passes through the ball-and-socket combination, and a third lumen passes through the tip, and wherein the first and second lumens are capable of simultaneously receiving a single guide wire therethrough.

13. The device of claim 11, wherein the tip has proximal and distal portions, the proximal portion being adjacent to the ball-and-socket combination and the distal portion being curved.

14. The device of claim 11, wherein the tip revolves around a ball of the ball-and-socket combination.

15. The device of claim 11, wherein each of the tip end surface and the end surface of the distal portion of the shaft is oriented at an oblique angle relative to the longitudinal axis of the shaft.

16. The device of claim 11, further comprising:
a locking mechanism attached to the shaft, the locking mechanism including an elongated member movable in the shaft between a retracted position and an extended position, and a plurality of apertures in the tip corresponding to various positions of the tip relative to the shaft, the elongated member in the extended position being receivable in one of the apertures to fix the tip in a first position relative to the shaft, the elongated member in the extended position being receivable in another of the apertures to fix the tip in a second position relative to the shaft, and the elongated member in the retracted position being free of any of the apertures to permit rotation of the tip relative to the shaft.

17. The device of claim 16, further comprising a spring disposed on the elongated member for biasing the elongated member to the extended position.

18. The device of claim 11, wherein the tip is rotatable only about the rotation axis.

19. The device of claim 11, wherein the tip is sized to fit within an artery such that rotation of the shaft does not rotate the tip.

20. A device for delivering an implantable medical apparatus into a patient, the device comprising:
a shaft having proximal and distal ends and a longitudinal axis, the distal end having a surface disposed at an oblique angle relative to the longitudinal axis of the shaft;
a tip operatively connected to the distal end of the shaft, the tip having a proximal end, a distal end and a longitudinal axis, the proximal end of the tip having a surface disposed at an oblique angle relative to the longitudinal axis of the tip, the proximal end surface of the tip being in mating engagement with the distal end surface of the shaft, the tip having a rotation axis perpendicular to the distal end surface of the shaft and the proximal end surface of the tip so that the tip is rotatable from a first position in which the longitudinal axis of the tip is collinear with the longitudinal axis of the shaft to a second position in which the longitudinal axis of the tip is oriented at an oblique angle relative to the longitudinal axis of the shaft; and a sheath movable relative to the tip between a first condition in which the sheath is adapted to surround the medical apparatus and a second condition in which the sheath is adapted to expose the medical apparatus for deployment, wherein the sheath is movable distally away from the distal end of the shaft and the tip is sized to fit within an artery such that rotation of the shaft does not rotate the tip.

* * * * *